United States Patent
Chaparian et al.

(10) Patent No.: US 6,875,582 B1
(45) Date of Patent: Apr. 5, 2005

(54) METHODS AND TARGETS OF ANTIBIOTIC RESISTANCE

(75) Inventors: Michael G. Chaparian, Chandler, AZ (US); Abul Azad, Dublin, OH (US)

(73) Assignee: OmniScience Pharmaceuticals, Inc., Worcester, MA (US)

(*) Notice: Subject to any disclaimer, the term of this patent is extended or adjusted under 35 U.S.C. 154(b) by 464 days.

(21) Appl. No.: 10/069,490

(22) PCT Filed: Aug. 18, 2000

(86) PCT No.: PCT/US00/40676

§ 371 (c)(1),
(2), (4) Date: Feb. 15, 2002

(87) PCT Pub. No.: WO01/12842

PCT Pub. Date: Feb. 22, 2001

Related U.S. Application Data (60) Provisional application No. 60/149,761, filed on Aug. 19, 1999.

(51) Int. Cl.[7] .............................. C12Q 1/02; C12Q 1/68; C12N 15/00
(52) U.S. Cl. .............................. 435/29; 435/6; 435/440; 435/441
(58) Field of Search .............................. 435/29, 6, 440, 435/441

(56) References Cited

U.S. PATENT DOCUMENTS

| | | | |
|---|---|---|---|
| 3,791,932 A | 2/1974 | Schuurs et al. | 435/4 |
| 3,839,153 A | 10/1974 | Schurrs et al. | 435/4 |
| 3,850,578 A | 11/1974 | McConnell | 435/4 |
| 3,850,752 A | 11/1974 | Schuurs et al. | 435/4 |
| 3,853,987 A | 12/1974 | Dreyer | 435/4 |
| 3,867,517 A | 2/1975 | Ling | 435/4 |
| 3,879,262 A | 4/1975 | Schurrs et al. | 435/4 |
| 3,901,654 A | 8/1975 | Gross | 435/4 |
| 3,935,074 A | 1/1976 | Rubenstein et al. | 435/4 |
| 3,984,533 A | 10/1976 | Uzgiris | 435/4 |
| 3,996,345 A | 12/1976 | Ullman et al. | 435/4 |
| 4,034,074 A | 7/1977 | Miles | 435/4 |
| 4,098,876 A | 7/1978 | Piasio et al. | 435/4 |
| 4,528,773 A | 7/1985 | Hickok | 47/58 |
| 4,666,828 A | 5/1987 | Gusella | 435/6 |
| 4,683,202 A | 7/1987 | Mullis | 435/91 |
| 4,736,866 A | 4/1988 | Leder et al. | 800/999.9 |
| 4,801,531 A | 1/1989 | Frossard | 435/6 |
| 4,879,219 A | 11/1989 | Wands et al. | 435/7 |
| 5,011,771 A | 4/1991 | Bellet et al. | 435/7 |
| 5,175,383 A | 12/1992 | Leder et al. | 800/2 |
| 5,175,384 A | 12/1992 | Krimpenfort et al. | 800/2 |
| 5,192,659 A | 3/1993 | Simons | 435/6 |
| 5,221,778 A | 6/1993 | Byrne et al. | 800/2 |
| 5,272,057 A | 12/1993 | Smulson et al. | 435/6 |
| 5,281,521 A | 1/1994 | Trojanowski et al. | 435/7.5 |

(Continued)

FOREIGN PATENT DOCUMENTS

| | | |
|---|---|---|
| WO | WO/93/14200 | 7/1993 |
| WO | WO/94/06908 | 3/1994 |
| WO | WO94/23049 | 10/1994 |
| WO | WO/94/28123 | 12/1994 |
| WO | WO 01/012842 A1 * | 2/2001 |

OTHER PUBLICATIONS

Osuna et al, Protein engineering, V. 15(6), pp. 463–70, (Jun. 2002) (Abstract Only).*

(Continued)

*Primary Examiner*—Louise N. Leary
(74) *Attorney, Agent, or Firm*—Kohn & Associates, PLLC (57) ABSTRACT

The present invention provides for a method of evolving and selecting cells resistant to a selective agent by inducing directed evolution in continuous culture while applying both a mutagenic and selective agent to the cells to determine the cells having resistance. This also provides a method of generating mutant drug targets useful for screening for effective compounds. The Figure is a generalized schematic diagram of a chemostat of the present invention

19 Claims, 3 Drawing Sheets

A, air pump
C, growing culture
D, air exit port
F, filter
G, gang valve
H, water humidification flask
I, input chamber
K, heating tape
M, fresh medium
O, siphon
P, peristaltic pump
W, waste

U.S. PATENT DOCUMENTS

| | | | |
|---|---|---|---|
| 5,288,846 A | 2/1994 | Quertermous et al. | 435/172.3 |
| 5,298,422 A | 3/1994 | Schwartz et al. | 435/320.1 |
| 5,347,075 A | 9/1994 | Sorge | 800/2 |
| 5,360,735 A | 11/1994 | Weinshank et al. | 435/240.2 |
| 5,387,742 A | 2/1995 | Cordell | 800/2 |
| 5,464,764 A | 11/1995 | Capecchi et al. | 435/172.3 |
| 5,487,992 A | 1/1996 | Capecchi et al. | 435/172.3 |
| 5,652,098 A | 7/1997 | Freyer | 435/6 |
| 6,720,142 B1 * | 4/2004 | Hall | 435/6 |

OTHER PUBLICATIONS

Ausubel et al., "Current Protocols in Molecular Biology," *John Wiley & Sons* (1989).

Birren et al., "Genome Analysis: A Laboratory Manual Series," vols. 1–4, *Cold Spring Harbor Lab Press* (1998).

Borrebaeck, "Antibody Engineering—A Practical Guide.".

Burke and Olson, "Preparation of Clone Libraries in Yeast Artifical–Chromosome Vectors" in *Methods in Enzymology*, vol. 194, "Guide to Yeast Genetics and MOlecular Biology," eds. C. Guthrie and G. Fink, Academic Press, Inc., Chap. 17, 251–270 (1991).

Capecchi, "Altering the genome by homologous recombination," *Science*, 244:1288–1292 (1989).

Cregg JM, Vedvick TS, Raschke WC "Recent Advances in the Expression of Foreign Genes in *Pichia pastoris*," *Bio/Technology*, 11:905–910 (1993).

Davies et al., "Targeted alterations in yeast artifical chromsomes for inter–species gene transfer," *Nucleic Acids Research*, 20(11):2693–2698 (1992).

Dickinson et al., "High frequency gene targeting using insertional vectors," *Human Molecular Genetics*, 2(8):1299–1302 (1993).

Duff and Lincoln, "Insertion of a pathogenic mutation into a yeast artificial chromosome containing the human APP gene and expression in ES cells," *Research Advances in Alzheimer's Disease and Related Disorders* (1995).

Gilboa, E, Eglitis, MA, Kantoff, PW, Anderson, WF, "Transfer and expression of clones genes using retroviral vectors," *BioTechniques* 4(6):504–512 (1986).

Harlow and Lane, "Antibodies: A Laboratory Manual," *Cold Spring Harbor Laboratory* (1988).

Huston et al., "Protein engineering of single–chain Fv analogs and fusion proteins," in *Methods in Enzymology* (JJ Langone, ed.; Academic Press, New York, NY) 203:46–88 (1991).

Huxley et al., "The human HPRT gene of a yeast artificial chromosome is functional when transferred to mouse cells by cell fusion," *Genomics*, 9:742–750 (1991).

Jakobovits et al., "Germ–line transmission and expression of a human–derived yeast artifical chromsome," *Nature*, 362:255–261 (1993).

Johnson and Bird, "Construction of single–chain Fvb derivatives of monoclonal antibodies and their production in *Escherichia coli*," in *Methods in Enzymology* (JJ Langon, ed.; Academic Press, New York, NY) 203:88–99 (1991).

Lamb et al., "Introduction and expression of the 400 kilobas precursor amyloid protein gene in transgenic mice," *Nature Genetics*, 5:22–29 (1993).

Marshak et al., "Strategies for Protein Purification and Characterization," *A Laboratory Course Manual* (1996).

Mernaugh and Mernaugh, "An overview of phage–displayed recombinant antibodies" in *Molecular Methods In Plant Pathology* (RP Singh and US Singh, eds., CRC Press Inc., Boca Raton, FL), 359–365 (1995).

Mishell and Shiigi, "Selected Methods in Cellular Immunology," *W.H. Freeman & Co.* (1980).

PCR Protocols "A Guide to methods and Applications," *Academic Press* (1990).

Pearson and Choi, "Expression of the human b–amyloid precursor protein gene from a yeast artificial chromosome in transgenic mice," *Proc. Natl. Acad. Sci. USA*, 90:10578–82 (1993).

Rothstein, "Targeting, disruption, replacement, and allele rescue: integrative DNA transformation in yeast" in *Methods in Enzymology*, "Guide to Yeast Genetics and Molecular Biology," eds. C. Guthrie and G. Fink, Academic Press, Inc., Chap. 19, 194:281–301 (1991).

Sambrook et al., "Molecular Cloning: A Laboratory Manual," *Cold Spring Harbor Lab Press* (1989).

Schedl et al., "A yeast artifical chromsome covering the tyrosinase gene confers copy number–dependent expression in transgenic mice," *Nature*, 362:258–261 (1993).

Stites et al., "Basic and Clinical Immunology," *Appletion & Lange*, $8^{th}$ Ed. (1994).

Strauss et al., "Germ line transmission of a yeast artifical chromosome spanning the murine $a_1$ (I) collagen locus," *Science*, 259:1904–1907 (1993).

Bertino, Joseph, et al., Drug resistant cells as targets for new therapies, Leukemia: Recent Advances in Biology and Treatment, pp. 529–536, Alan R. Liss, Inc. (1985).

Dykhuizen, Daniel, Chemostates used for studying natural selection and adaptive evolution, Methods in Enzymology, vol. 224, Academic Press, Inc. (1993).

Ferrero, Lucy, et al., Analysis of gyrA and grlA mutations in stepwise–selected ciprofloxacin–resistant mutants of staphylococcus aureas, Antimicrobial Agents and Chemotherapy, Jul. 1995, p. 1554–1558.

Kolterman, et al., Principles and methods of evolutionary biotechnology, Biophysical Chemistry 66:159–177 Elsevier Science B.V. (1997).

Wiebe, Marilyn, et al., Use of a series of chemostate cultures to isolate "improved" variants of the Quorn mycoprotein fungus, Fusarium graminearum A3/5, Miccrobiology (1994) 140:3015–3021.

Wiebe et al; Microbiology, V. 140; pp. 3015–30–21; (1994). □□.

Bertino et al; Recent Advances in Biology and Treatment; pp. 529–536; (1985).

* cited by examiner

A, air pump
C, growing culture
D, air exit port
F, filter
G, gang valve
H, water humidification flask
I, input chamber
K, heating tape
M, fresh medium
O, siphon
P, peristaltic pump
W, waste

FIGURE 1A

FIGURE 1B

Figure 2
Directed Evolution of the Quinolone-Resistance Determinant Region
(QRDR) of the gyrA Gene Sequence of E. coli*

```
                      G⁸¹ D⁸² S⁸³        D⁸⁷
                      ‾‾‾‾‾‾‾‾‾‾‾        ‾‾‾
E.coli 11775(WT)  TTGGTGACGTAATCGGTAAATACCATCCCATGGTGACTTATGACACGATCGGCGGTTACGGCAGCCATTCTCGCTGCGTTACATGCTGGTGACGGTC
NX-E9             TTGGTGACGTAATCGGTAAATACCATCCATCCCATGGTGACTCGGCGGTGACTTATACACGATCGGCCAGCCATTCTCGCTGCGTTACATGCTGGTAGACGGTC
NX-E10            TTGGTGACGTAATCGGTAAATACCATCCCATGGTGACTTGGCGGTGACTTGGCGGTGACTTATGACACGATCGGCCAGCCATTCTCGCTGCGTACATGCTGGTAGACGGTC
NX-N6             TTGGTGACGTAATCGGTAAATACCATCCCATGGTGACTTGGCGGTGACTTGGCGGTTTATGACACGATCGGCCAGCCATTCTCGCTGCGTGCGTTACATGCTGGTAGACGGTC
NX-M3             TTGGTGACGTAATCGGTAAATACCATCCCATGGTGACTCGGCGGTGACTCGGCGGTTATGCACGATCGGCCAGCCATTCTCGCTGTCGTTACATGCTGGTAGACGGTC
NX-M5             TTGGTGACGTAATCGGTAAATACCATCCCATGGTGACTCGGCGGTGACTCGGCGGTTATAACACGATCGGCCAGCCATTCTCGCTGTCGTTACATGCTGGTAGACGGTC
NX-M6             TTGGTGACGTAATCGGTAAATACCATCCCATGGTGACTGACTCGGCGGTGACTCGGCGGTGACTTATGACACGATCGGCCAGCCATTCTCGCTGTCGTTACATGCTGGTAGACGGTC
D7NX-E1           TTGGTGACGTAATCGGTAAATACCATCCATCCCATGGTGACTGGTGACTTGGCGGTGATTGGCGGTTATGACACGATCGACACGATCGGCCAGCCATTCTCGCTGTCGTTACATGCTGGTAGACGGTC
D7NX-E2           TTGGTGACGTAATCGGTAAATACCATCCCATGGTGACTCGGCGGTGACTGGCGGTTATGACACGATCGACACGATCGGCCAGCCATTCTCGCTGCGTTACATGCTGGTAGACGGTC
D3NX-E5           TTGGTGACGTAATCGGTAAATACCATCCCATGGTGACTCGGCGGTGACTCGGCGGTTATGACACGATCGACACGATCGGCCAGCCATTCTCGCTGCGTTACATGCTGGTAGACGGTC
D3NX-E6           TTGGTGACGTAATCGGTAATCGTAAATACCATCCCATGGTGACTCGGCGGTGACTCGGCGGTTATGACACGATCGACACGATCGGCCAGCCATTCTCGCTGCGTTACATGCTGGTAGACGGTC
D2C2-a            TTGGTGACGTAATCGGTAAATACCATCCCATGGTGACTCGGCGGTGACTCGGCGGTATGACGGTATGACGGTTATGACACGATCGACACGATCGGCCAGCCATTCTCGCTGCGTTACATGCTGGTAGACGGTC
D2C2-h            TTGGTGACGTAATCGGTAAATACCATCCCATGGTGACTCGGCGGTGACTCGGCGGTGACTTATGACACGATCCACACGATCGGCCAGCCATTCTCGCTGCGTTACATGCTGGTAGACGGTC
D2C2-i            TTGGTGACGCAATCGGTAAATACCATCCCATGGTGACGTAACTCGGCGGCGGTTATGACACGATCTATGACACGATCGCCATGGCGCAGCCATTCTCGCTGCGTACATGCTGGTAGACGGTC
```

* G = Glycine, D = Aspartic Acid, S = serine (amino acid positions are numbered as superscripts).
Single or double base pair point mutations are shown in blue letters and the mis-matching bases are shown in red letters.

METHODS AND TARGETS OF ANTIBIOTIC RESISTANCE

CROSS REFERENCE TO RELATED APPLICATIONS

The present application is a National Phase Concerning a Filing Under 35 U.S.C. 371, claiming the benefit of priority of PCT/US00/40676, filed Aug. 18, 2000, which claims the benefit of priority of U.S. Provisional Ser. No. 60/149,761, filed Aug. 19, 1999 both of which are incorporated herein by reference.

BACKGROUND OF THE INVENTION

1. Field of the Invention

Generally, the present invention relates to methods and materials for the discovery and characterization of molecular mechanisms of drug resistance. More specifically, the present invention relates to methods and materials for the discovery and characterization of molecular mechanisms of drug resistance using directed evolution.

2. Description of Related Art

Drug resistance, especially that of antiinfective and anticancer drugs, is an extremely important aspect of the clinical use and efficacy of therapeutic compounds in the treatment of human and animal diseases. Drug resistance necessitates affirmative treatments which can be less effective and more costly. Moreover, the rapidly increasing rate of reemergence of once controlled clinical infections is seriously eroding the repertoire of effective antibiotics. For example, many common pediatric antibiotics, such as amoxicillin, have been rendered much less effective against such common infections as otitis media due to emerging resistance over the past decade. Alternative therapeutics, when available, are often much more expensive than the first line drug. Likewise, tumor cells of patients undergoing cancer treatment often become resistant to the anticancer drugs being used.

A key in determining the cause of resistance is often found in an analysis of the drug target proteins of the pathogenic organism. Mutation of the drug target protein is responsible for much of the rapidly increasing rate of clinical antibiotic resistance. This is attributable to the large number and variety of antibiotics that target cellular proteins. Likewise, changes in the target protein structure, as a result of point mutations in the gene, results in loss of binding and efficacy of the antibiotic. This has been widely observed in clinical isolates for nearly all antibiotics targeting cellular proteins.

The amino acid sequence of a protein determines its three-dimensional (3D) structure, which in turn determines protein function (EPST63, ANFI73). Shortle (SHOR85), Sauer and colleagues (PAKU86, REID88a), and Caruthers and colleagues (EISE85) have shown that some residues on the polypeptide chain are more important than others in determining the 3D structure of a protein. The 3D structure is essentially unaffected by the identity of the amino acids at some loci, while at other loci, only one or a few types of amino-acid is allowed. In most cases, the loci is where wide variety is allowed have the amino acid side-chain group directed toward the solvent. Loci where limited variety is allowed frequently have the sidechain group directed toward other parts of the protein. Thus substitutions of amino acids that are exposed to solvent are less likely to affect the 3D structure than are substitutions at internal loci. (See also SCHU79, p169–171 and CREI84, p239–245, 314–315).

The secondary structure (helices, sheets, turns, loops) of a protein is determined mostly by local sequence. Certain amino acids have a propensity to appear in certain "secondary structures," they are found from time to time in other structures, and studies of pentapeptide sequences found in different proteins have shown that their conformation varies considerably from one occurrence to the next (KABS84, ARGO87). As a result, a priori design of proteins to have a particular 3D structure is difficult.

Several researchers have designed and synthesized proteins de novo (MOSE83, MOSE87, ERIC86). These designed proteins are small and most have been synthesized in vitro as polypeptides rather than genetically. Hecht et al. (HECH90) have produced a designed protein genetically. Moser, et al. state that design of biologically active proteins is currently impossible.

Many proteins bind non-covalently but very tightly and specifically to some other characteristic molecules (SCHU79, CREI84). In each case, the binding results from complementarity of the surfaces that come into contact: bumps fit into holes, unlike charges come together, dipoles align, and hydrophobic atoms contact other hydrophobic atoms. Although bulk water is excluded, individual water molecules are frequently found filling space in intermolecular interfaces, these waters usually form hydrogen bonds to one or more atoms of the protein or to other bound water. Thus proteins found in nature have not attained, nor do they require, perfect complementarity to bind tightly and specifically to their substrates. Only in rare cases is there essentially perfect complementarity; then the binding is extremely tight (as for example, avidin binding to biotin).

"Protein engineering" is the art of manipulating the sequence of a protein in order to alter its binding characteristics. The factors affecting protein binding are known, (CHOT75, CHOT76, SCHU79, p98–107, and CREI84, Ch8), but designing new complementary surfaces has proved difficult. Although some rules have been developed for substituting side groups (SUTC87b), the side groups of proteins are floppy (i.e. can move from side to side) and it is difficult to predict what conformation a new side group will take. Further, the forces that bind proteins to other molecules are all relatively weak and it is difficult to predict the effects of these forces.

Recently, Quiocho and collaborators (QUIO87) elucidated the structures of several periplasmic binding proteins from Gram-negative bacteria. They found that the proteins, despite having low sequence homology and differences in structural detail, have certain important structural similarities. Based on their investigations of these binding proteins, Quiocho et al. suggest it is unlikely that, using current protein engineering methods, proteins can be constructed with binding properties superior to those of proteins that occur naturally.

Nonetheless, there have been some isolated successes. Wilkinson et al. (WILK84) reported that a mutant of the tyrosyl tRNA synthetase of Bacillus stearothermophilus with the mutation $Thr_{51} \rightarrow Pro$ exhibits a 100-fold increase in affinity for ATP Tan and Kaiser (TANK77) and Tschesche et al. (TSCH87) showed that changing a single amino acid in mini-protein greatly reduces its binding to trypsin, but that some of the mutants retained the parental characteristic of binding to an inhibiting chymotrypsin, while others exhibited new binding to elastase. Caruthers and others (EISE85) have shown that changes of single amino acids on the surface of the lambda Cro repressor greatly reduce its affinity for the natural operator $O_R$ 3, but greatly increase the binding of the mutant protein to a mutant operator. Changing three residues in subtilisin from Bacillus amyloliquefaciens to be the same as the corresponding residues in subtilisin from B. licheniformis produced a protease having nearly the same activity as the latter subtilisin, even though 82 amino acid sequence differences remained (WELL87a). Insertion of DNA encoding 1B amino acids (corresponding to Pro-Glu-Dynorphin-Gly) into the *E. coli* phoA gene so that the additional amino acids appeared within a loop of the alkaline phosphatase protein resulted in a chimeric protein having both phoA and dynorphin activity (FREI9O). Thus, changing the surface of a binding protein can alter its specificity without abolishing binding activity.

Early techniques of mutating proteins involved manipulations at the amino acid sequence level. In the semi-synthetic method (TSCH87), the protein was cleaved into two fragments, a residue removed from the new end of one fragment, the substitute residue added on in its place, and the modified fragment joined with the other, original fragment. Alternatively, the mutant protein could be synthesized in its entirety (TANK77).

Erickson et al. suggested that mixed amino acid reagents could be used to produce a family of sequencerelated proteins which could then be screened by affinity chromatography (ERIC86). They envision successive rounds of mixed synthesis of variant proteins and purification by specific binding. They do not discuss how residues should be chosen for variation. Because proteins cannot be amplified, the researchers must sequence the recovered protein to learn which substitutions improve binding. The researchers must limit the level of diversity so that each variety of protein is present in sufficient quantity for the isolated fraction to be sequenced.

With the development of recombinant DNA techniques, it became possible to obtain a mutant protein by mutating the gene encoding the native protein and then expressing the mutated gene. Several mutagenesis strategies are known. One, "protein surgery" (DILL87), involves the introduction of one or more predetermined mutations within the gene of choice. A single polypeptide of completely predetermined sequence is expressed, and its binding characteristics are evaluated.

At the other extreme is random mutagenesis by means of relatively nonspecific mutagens such as radiation and various chemical agents. See Ho et al. (HOCJ85) and Lehtovaara, E. P. Appin. 285,123.

It is possible to randomly vary predetermined nucleotides using a mixture of bases in the appropriate cycles of a nucleic acid synthesis procedure. The proportion of bases in the mixture, for each position of a codon, determines the frequency at which each amino acid occurs in the polypeptides expressed from the degenerate DNA population. Oliphant et al. (OLIP86) and Oliphant and Struhl (OLIP87) have demonstrated ligation and cloning of highly degenerate oligonucleotides, which were used in the mutation of promoters. They suggested that similar methods could be used in the variation of protein coding regions. They do not say how one should: a) choose protein residues to vary, or b) select or screen mutants with desirable properties. Reidhaar-Olson and Sauer (REID88a) have used synthetic degenerate oligo-nts to vary simultaneously two or three residues through all twenty amino acids. See also Vershon et al. (VERS86a; VERS86b). Reidhaar-Olson and Sauer do not discuss the limits on how many residues could be varied at once nor do they mention the problem of unequal abundance of DNA encoding different amino acids. They looked for proteins that either had wild-type dimerization or that did not dimerize. They did not seek proteins having novel binding properties and did not find any. This s approach is likewise limited by the number of colonies that can be examined (ROBE86).

To the extent that this prior work assumes that it is desirable to adjust the level of mutation so that there is one mutation per protein, many desirable protein alterations require multiple amino acid substitutions and thus are not accessible through single base changes or even through all possible amino acid substitutions at any one residue.

Ferenci and collaborators have published a series of papers on the chromatographic isolation of mutants of the maltose-transport protein LamB of *E. coli* (FERE82a, FERE82b, FERE83, FERE84, CLUN84, HEIN87 and is papers cited therein). The mutants were either spontaneous or induced with nonspecific chemical mutagens. Levels of mutagenesis were picked to provide single point mutations or single insertions of two residues. No multiple mutations were sought or found.

While variation was seen in the degree of affinity for the conventional LamB substrates maltose and starch, there was no selection for affinity to a target molecule not bound at all by native LamB, and no multiple mutations were sought or found. FERE84 speculated that the affinity chromatographic selection technique could be adapted to development of similar mutants of other "important bacterial surface located enzymes", and to selecting for mutations which result in the relocation of an intracellular bacterial protein to the cell surface. Ferenci's mutant surface proteins would not, however, have been chimeras of a bacterial surface protein and an exogenous or heterologous binding domain.

Ferenci also taught that there was no need to clone the structural gene, or to know the protein structure, active site, or sequence.

Ferenci did not limit the mutations to particular loci or particular substitutions. Ferenci does not suggest that surface residues should be preferentially varied. In consequence, Ferenci's selection system is much less efficient than that disclosed herein.

A number of researchers have directed unmutated foreign antigenic epitopes to the surface of bacteria or phage, fused to a native bacterial or phage surface protein, and demonstrated that the epitopes were recognized by antibodies. Thus, Charbit, et al. (CHAR86) genetically inserted the C3 epitope of the VP1 coat protein of poliovirus into the LamB outer membrane protein of *E. coli*, and determined immunologically that the C3 epitope was exposed on the bacterial cell surface. Charbit, et al. (CHAR87) likewise produced chimeras of LamB and the A (or B) epitopes of the preS2 region of hepatitis B virus.

A chimeric LacZ/OmpB protein has been expressed in *E. coli* and is, depending on the fusion, directed to either the outer membrane or the periplasm (SILH77). A chimeric LacZ/OmpA surface protein has also been expressed and displayed on the surface of *E. coli* cells (Weinstock et al., WEIN83). Others have expressed and displayed on the surface of a cell chimeras of other bacterial surface proteins, such as *E. coli* type 1 fimbriae (Hedegaard and Klemm (HEDE89)) and Bacterioides nodusus type 1 fimbriae (Jennings et al., JENN89). In none of the recited cases was the inserted genetic material mutagenized.

Dulbecco (DULB86) suggests a procedure for incorporating a foreign antigenic epitope into a viral surface protein so that the expressed chimeric protein is displayed on the surface of the virus in a manner such that the foreign epitope is accessible to antibody. In 1985 Smith (SMIT85) reported inserting a nonfunctional segment of the EcoRI endonuclease gene into gene III of bacteriophage f1, "in phase". The gene III protein is a minor coat protein necessary for infectivity. Smith demonstrated that the recombinant phage were adsorbed by immobilized antibody raised against the EcoRI endonuclease, and could be eluted with acid. De la Cruz et al (DELA88) have expressed a fragment of the repeat region of the circumsporozoite protein from Plasmodium falciparum on the surface of M13 as an insert in the gene III protein. They showed that the recombinant phage were both antigenic and immunogenic in rabbits, and that such recombinant phage could be used for B epitope mapping. The researchers suggest that similar recombinant phage could be used for T epitope mapping and for vaccine development.

McCafferty et al. (MCCA90) expressed a fusion of an Fv fragment of an antibody to the Nerminal of the pill protein. The Fv fragment was not mutated. F. Epitope Libraries on Fusion Phage Parmley and Smith (PARM88) suggested that an epitope library that exhibits all possible hexapeptides could be constructed and used to isolate epitopes that bind to antibodies. In discussing the epitope library, the authors did not suggest that it was desirable to balance the representation of different amino acids. Nor did they teach that the insert should encode a complete domain of the exogenous protein. Epitopes are considered to be unstructured peptides as opposed to structured proteins.

Another problem with the Scott and Smith, Cwirla et al., and Devlin et al., libraries was that they provided a highly biased sampling of the possible amino acids at each position. Their primary concern in designing the degenerate oligonucleotide encoding their variable region was to ensure that all twenty amino acids were encodable at each position; a secondary consideration was minimizing the frequency of occurrence of stop signals. Consequently, Scott and Smith and Cwirla et al. employed NNK (N=equal mixture of G, A, T, C; K=equal mixture of G and T) while Devlin et al. used NNS (S=equal mixture of G and C). There was no attempt to minimize the frequency ratio of most favoretoleast favored amino acid, or to equalize the rate of occurrence of acidic and basic amino acids.

Devlin et al. characterized several affinity-selected streptavidin-binding peptides, but did not measure the affinity constants for these peptides. Cwirla et al. did determine the affinity constant for his peptides, but were disappointed to find that his best hexapeptides had affinities (350–300 nM), "orders of magnitude" weaker than that of the native Met-enkephalin epitope (7 nM) recognized by the target antibody. Cwirla et al. speculated that phage bearing peptides with higher affinities remained bound under acidic elution, possibly because of multivalent interactions between phage (carrying about 4 copies of pill) and the divalent target lgG. Scott and Smith were able to find peptides whose affinity for the target antibody (A2) was comparable to that of the reference myohemerythrin epitope (50 nM). However, Scott and Smith likewise expressed concern that some high-affinity peptides were lost, possibly through irreversible binding of fusion phage to target. G. Non-Commonly Owned Patents and Applications Naming Robert Ladner as an Inventor.

Ladner, U.S. Pat. No. entitled, "Computer Based System and Method for Determining and Displaying Possible Chemical Structures for Converting Double or Multiple-Chain Polypeptides to Single-Chain Polypeptides" describes a design method for converting proteins composed of two or more chains into proteins of fewer polypeptide chains, but with essentially the same 3D structure. There is no mention of variegated DNA and no genetic selection. Ladner and Bird, WO88101649 (Publ. Mar. 10, 1988) disclose the specific application of computerized design of linker peptides to the preparation of single chain antibodies.

Ladner, Glick, and Bird, WO88/06630 (publ. 7 Sep. 1988 and having priority from U.S. application Ser. No. 07/021, 046, assigned to Genex Corp.) (LGB) speculate that diverse single chain antibody domains (SCAD) can be screened for binding to a particular antigen by varying the DNA encoding the combining determining regions of a single chain antibody, subcloning the SCAD gene into the gpV gene of phage lambda so that a SCAD/gpV chimera is displayed on the outer surface of phage lambda, and selecting phage which bind to the antigen through affinity chromatography. The only antigen mentioned is bovine growth hormone. No other binding molecules, targets, carrier organisms, or outer surface proteins are discussed. Nor is there any mention of the method or degree of mutagenesis. Furthermore, there is no teaching as to the exact structure of the fusion nor of how to identify a successful fusion or how to proceed if the SCAD is not displayed.

Additionally, other prior art does not disclose any correlation between any of these mutations and any cellular activity. However, it has been found that the sites of antibiotic activity within target microorganisms are generally defined, and also give rise to resistance through adaptive mutations that confer resistance. Clonal propagation can also account for the spread of resistant infections in addition to independently emerging mutants.

Specifically, it would be useful to establish a correlation between these mutations and cellular activity. Also, useful is a method which shows how to implement the principles of directed evolution to evolve and discover drug resistance mechanisms and resistance conferring molecules from a presently susceptible microorganism. This would allow for predicting the time of clinical efficacy of a drug prior to its wide-spread clinical use, and the discovery and characterization of the molecule that eventually confers resistance to the target microorganism. This resistance conferring molecule would also be useful for drug screening for subsequent generation of agents for future clinical use.

SUMMARY OF THE INVENTION

According to the present invention, there is provided a method of evolving and selecting cells resistant to a selective agent by inducing directed evolution in continuous culture while applying both a magnetic and selective agent to the cells to determine the cells having resistance. This also provides a method of generating mutant drug targets useful for screening for effective compounds.

DESCRIPTION OF THE DRAWINGS

Other advantages of the present invention are readily appreciated as the same becomes better understood by reference to the following detailed description when considered in connection with the accompanying drawings:

FIG. 1A is a generalized schematic diagram of a chemostat of the present invention;

FIG. 1B is a schematic diagram of a specific chemostat of the present invention; and FIG. 2 is a sequence alignment of the quinolone resistance determining region from resistant mutants generated with the present invention compared to the wild type.

DETAILED DESCRIPTION OF THE INVENTION

The present invention is directed to a method for evolving and/or selecting for microorganisms from a susceptible culture or sample, that are resistant to one or more therapeutic agents. This agent is typically an antibiotic or anticancer compound. The method relies upon the principles of directed evolution and is specifically implemented through continuous culture in the presence of both selective agent (antibiotic) and mutagen.

Figure 1A:
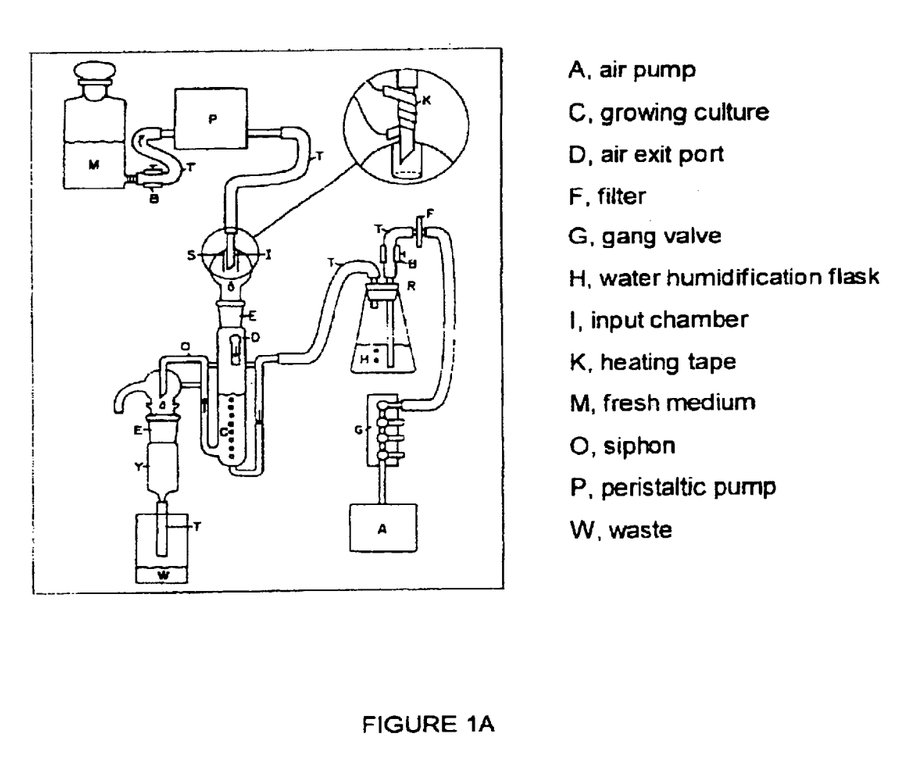
Figure 1B:
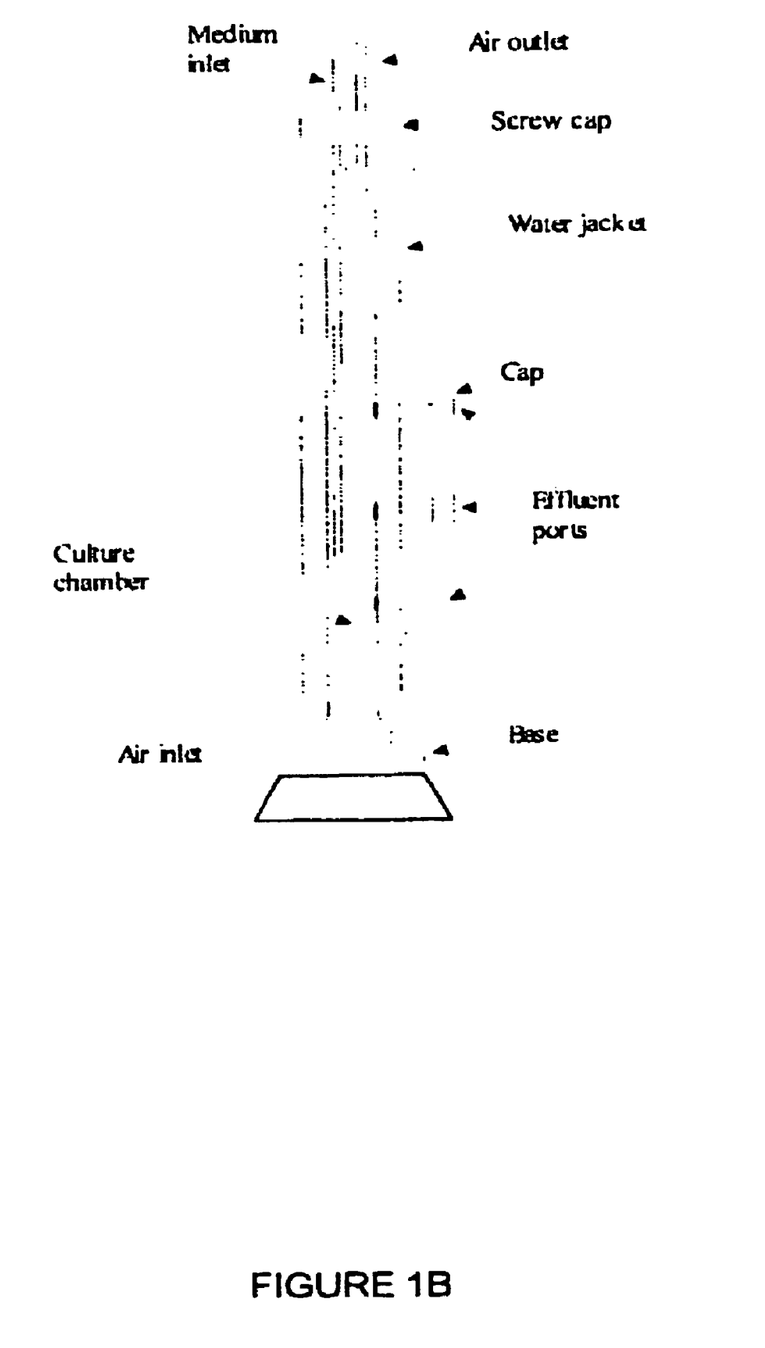

A "chemostat" as used herein is meant to include any apparatus which properly controls the environment such that bacterial culture is maintained in a continuous state of cell division. Any chemostat can be used that is appropriate for the experimental conditions at hand as are known to those of skill in the art. A generalized schematic is shown in FIG. 1A (Dykhuizen, 1993), and can be of simple, ready-made and/or of custom design. A proprietary design for a very versatile, variable volume chemostat is shown in FIG. 1B.

The term "selective agent" as used herein is meant to include any chemotherapeutics or any other compound that can act to permit phenotypic or genotypic differentiation between mutant and wild type cells. Additional examples would include industrial chemicals that can also be used as nutrients by microorganisms. Mutagens used in the present invention include Ethyl Methanesulfonate (EMS), 4Nitroquinoline-lxide (NQO), and N-Methyl-N'-Nitro-N-Nitrosoguanidine (MNNG), but can include any magnetic agent, physical or chemical, without departing from the disclosure of the present invention. For example, UV irradiation of a chemostatic culture, so specially constructed of UV transparent glass can be implemented. The design of the chemostat shown in FIG. 1B is especially amenable to this application due to the columnar shape and relatively light transparent culture vessel with the chemostat. However, any apparatus that can provide for continuous culture, including chemostats, nutristats, and fermentors, can be is used in the present invention.

In the practice of the present invention, the drug sensitive microorganism is cultured in a chemostat via continuous culture. The selective agent (e.g. antibiotic) is also added to the culture medium either continuously or in a stepwise manner. Additionally, mutagenic agents are added to the continuous culture at a concentration predetermined by a survivability vs. dose curve. The optimum concentration of mutagen produces the maximum number of non-lethal mutations.

The optimum concentration of mutagen is determined empirically by determining a survivability vs. dose curve. This concentration must be determined empirically for each pure strain or mixed culture used. In general, for stepwise mutagenesis and selection, the optimum concentration for many bacteria, including several strains of E. coli, is approximately 0.5–3% (v/v or w/w) for 20 to 120 minutes. Alternatively, the mutagen can be infused slowly and continuously into the continuous culture, with adjustments, if necessary, in reduced medium influx to compensate for decreasing numbers of cells in culture as a result of lethal mutations. This is also determined empirically from the survivability vs. dose curve.

A typical evolution/discovery chemostat consists of a 100 to 1000 ml culture grown for several generations to establish stability and equilibrium. Subsequently, mutagen is added to the chemostatic culture, as described in the preceding paragraph, to the predetermined concentration of mutagenic agent. Subsequently, antibiotic selection is commenced at a predetermined concentration (either step-wise or constant infusion). Typically, and as in the case of antibiotic used for selection, the selective agent concentration is titered to give a differential growth rate between wild type and resistant mutants.

While the presence of a selective agent in the culture provides an ongoing estimate of increasing resistance. a mare detailed analysis is provided by submitting a small portion of the culture to an antibiotic susceptibility test, such as a simple antibiotic gradient plate, at various times during directed evolution. Analyzing all the resistant colonies allows for the entire evolutionary spectrum of resistance to be determined. Control chemostats, lacking mutagen, are also monitored in this manner in order to differentiate emerging resistance caused by mutagenesis from clonal selection of preexisting variants (mutants). However, in either case, the present invention provides similar benefits in providing the isolation and characterization of resistant mutants, not otherwise available.

In an embodiment of the present invention, the use of a material that mimics a physiological attachment or colonization site in the chemostat can effect the rate of evolution and molecular mode of resistance. For example, the inclusion of a relatively small amount of glass or polystyrene beads, or biological matrix, increases the rate of mutant evolution and selection in the nalixidic acid/E. coli ATCC 11775 model system described above. Thus, the present invention is also useful for discovery and characterization of virulence mechanisms and determinants, and can have important applications in the area of biofilms as relevant to virulence.

The foregoing discussion, description, and examples are illustrative of particular embodiments of the invention, but are not meant to be limitations upon the practice thereof It is the following claims, including all equivalents, which define the scope of the invention.

EXAMPLES

General Methods

General methods in molecular biology: Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Maryland (1989) and in Perbal, *A Practical Guide to Molecular Cloning*, John Wiley & Sons, New York (1988), and in Watson et al., *Recombinant DNA*, Scientific American Books, New York and in Birren et al (ads) *Genome Analysis*: A Laboratory Manual Seies, Vols. 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (in-cell) PCR in combination with Flow Cytometry can be used for detection of cells containing specific DNA and mRNA sequences (Testoni et al, 1996, Blood 87:3822.)

Recombinant Protein Purification

Marshak et al, "Strategies for Protein Purification and Characterization. A laboratory course manual." CSHL Press, 1996.

General Methods in Microbiology

Standard microbiology techniques known in the art and not specifically described were generally followed as in Gerhardt et al. (Eds), *Methods for General and Molecular*

Biology, American Society for Microbiology, Washington D.C. (1994), and in Woodford et al. (Eds), *Molecular Bacteriology: Protocols and Clinical Applications*, Humana Press, Totowa, N.J. (1998) and in Demain et al. (Eds), *Manual of Industrial Microbiology and Biotechnology*, American Society for Microbiology, Washington D.C. (1986), and in Brock et al., *Biology of Microorganisms*, 5$^{th}$ Edition, Prentice Hall, New Jersey (1988).

EXAMPLE 1

The present invention has been used to evolve quinolone resistant is mutants from the antibiotic sensitive *E. coli* reference strain ATCC 11775 evolved with EMS mutagen in the presence of nalidixic acid as the selective agent, and to correlate the level of resistance with specific point mutations occurring within the quinolone resistance determining region (QRDR) of the gyrase A gene (gyrA).

Before proceeding to directed evolution, the survival rate of bacteria upon exposure to different concentrations of mutagens for varying periods of time was determined in growth medium, either LB or TS broth. Bacteria were grown in broth with shaking until they reached log to late log phase. Mutagen was added at this stage and the bacteria were allowed to grow for a specified period of time, depending on the type of mutagen. The mutagenic reaction was terminated by immediately washing and diluting the bacterial cells in suitable buffer or growth medium. The different dilutions of the cells were plated on agar medium to determine the surviving fractions of the cells, which were compared with the non-treated bacterial cell used as control for 100% survival.

The selected concentration of mutagens and the reaction period for *E. coli* ATCC 11775 resulting in an acceptable range of survival rates with reasonable mutational frequencies are shown in Table I.

Proprietary microcarrier spinner flask chemostats were used for continuous culture. Two hundred ml of LB or TS broth containing antifoam A (50 ppm concentration) was autoclaved in the chemostat flask with associated tubes and connectors attached to them. The chemostats were set up, by placing them on a multi-magnetic stirrer, and by connecting them to a constant water supply for providing constant temperature, to a vacuum pump through the waste-disposal reservoir, and to the medium reservoir through a controllable peristaltic pump. The starter culture of bacteria was inoculated into the flask through a sample port by using a 3.0-ml sterile syringe followed by washing the port with an aliquot of sterile broth. The culture was allowed to grow in batch mode with constant stirring until it reached log to late log is phase (usually 3.0 to 4.5 hours). At this stage, continuous culture mode was established by feeding the flask with a continuous supply of fresh medium from the reservoir. The flow rate was maintained so that the culture medium could be replaced with the fresh medium during the time period when the culture attains its log phase. $OD_{600}$ was monitored at regular intervals by withdrawing the culture through the sample port with a sterile syringe. The culture was, thus, allowed to maintain several generations at its log phase. Mutagen EMS (2% w/v) or MNNG (10 µg/ml) was added to the continuous culture through one of the infusion ports for a specific period, during which the chemostat was operated in batch mode (30 minutes for EMS and 10 minutes for MNNG). The continuous culture was resumed at a slightly higher flow rate to ensure washing of the mutagen from the chemostat before selection of the culture with the target antibiotic or inhibitor. Alternatively, a low dose or sublethal concentrations of mutagen (e.g., 0.1–0.5 µg MNNG/ml) was directly added to the medium reservoir in order to maintain the constant exposure of the mutagen in the continuous culture system. Antibiotic was also directly incorporated into the medium reservoir for the selection of mutants from the mutagenized culture after several generations, starting with the sub-lethal concentrations of antibiotic and then with the gradual increase of the antibiotic concentration, depending on the culture growth.

At 8–12 hour intervals a small aliquot of the culture was withdrawn from the chemostat, $OD_{600}$ was measured, and an aliquot of the culture was spread on an agar medium containing a gradient of the selective antibiotic (0–30 µg nalidixic acid/ml).

Antibiotic-resistant clones were selected at varying concentrations along the gradient and further analyzed by a standard antimicrobial disk-diffusion test (antibiogram) for extent of resistance phenotypes (whether partially or completely resistant). Genomic DNA from the selected mutant was prepared and used as template in a PCR designed to amplify the target resistance gene. The PCR product was sequenced directly and analyzed to detect the expected point mutations within the resistance-determining region (QRDR) (Table II). Sequences were routinely aligned and compared with the wild-type (non-mutated) gene or gene region (FIG. 2).

An *E. coli* strain 11775 was also subjected to mutagenesis by EMS in a chemostat continuous culture system and allowed to grow for seven days for over 400 generations. Culture was selected for $NA^R$ mutants on NA-containing gradient plate every 12 hours *E. coli* $NA^R$ clones, thus obtained, from different time-points were analyzed for their phenotype and genetic mutation, especially in the gyrA QRDR. Pont mutations in the QRDR of several selected $NA^R$ clones from different time-points (generations) are shown in Table III.

The regions of the gyrA QRDR sequence of *E. coli* 11775 $NA^R$ mutants, where the mutagen-induced point mutations were consistently observed are shown in FIG. 3. Importantly, controls were conducted in parallel, as described above, and confirmed that the resistant isolates were new mutants and not the result of selection of preexisting mutants.

Most importantly, this example of the present invention accurately mimics both the genotype and phenotype of the clinical resistant isolates (Weigel, L. M., et al., 1998). Nalixidic acid resistant mutants (e.g. NX-E09/11775 and NX-E09/11775) show the specific point mutations observed in several fluoroquinolone resistant clinical isolates (FIG. 2). This occurs in spite of mutagenesis occurring in a random fashion. Thus, the present invention is useful as a means to accurately discover and characterize, through directed evolution, resistance conferring molecular determinants.

EXAMPLE II

An additional demonstration of the method and materials embodying this invention comes from the application of the invention to the evolution of an extended spectrum beta-lactam resistant strain of *Klebsiella pneumoniae*. The development of extended spectrum P-Lactam resistant mutants of *K. pneumoniae* was carried out in similar manner as described in Example I. A clinical isolate, *K. pneumoniae* strain Tim 19, was found to contain the TEM-1 P-lactamase which conferred resistance to ampicillin (AM) and amoxicillin/clavulanate (AMC). However, this strain was sensitive to extended spectrum beta-lactams (ESBLS) such as cefotaxime (CTX), ceftazidime (CAZ), cefoxitin (FOX), aztreonum (ATM). This clinical strain was subjected to mutagenesis with MNNG in the continuous culture system for at least eight days under continuous mutagen and antibiotic infusion. ESBL resistant mutants were selected with CTX in the range of 2–550 µg/ml. Several $CTX^R$ mutants were obtained and analyzed for their multi-drug-resistance phenotypes (Table IV).

This example again demonstrates the utility of the present invention in providing the methods and materials to discover and characterize antibiotic resistance prior to clinical emergence.

In an embodiment of the present invention, the use of a material that mimics a physiological attachment or colonization site in the chemostat can effect the rate of evolution and molecular mode of resistance. For example, the inclusion of a relatively small amount of glass or polystyrene beads, or biological matrix, increases the rate of mutant evolution and selection in the nalixidic aid/E. coli ATCC 11775 model system described above. Thus, the present invention is also useful for discovery and characterization of virulence mechanisms and determinants, and can have important applications in the area of biofilms as relevant to virulence.

An important aspect of the utility of this invention is its ability to predict antibiotic resistance prior to clinical emergence. Prior to the development of the present invention, there had only been a single case where the molecular mechanism of resistance was predicted in vitro prior to this characterization from a clinical isolate (Arlet, G., et al., 1993). Most importantly, the present invention provides validated drug intervention targets, useful for screening in the development of next generation compounds. These targets can be either the actual mutant protein target or the resistant strain itself. Validated targets differ from putative or hypothetical targets in that they are proven to confer the observed resistance, and therefore, serve as useful intervention targets for future therapeutic development. Validated targets are provided through the practice of the present invention because directed evolution, mutation, and selection are conducted in vivo, and in the relevant biological host. This differs greatly from any form of in vitro mutagenesis or even evolution conducted in a non-relevant host (nonclinical), and is likely the reason that predicting the molecular mechanism of clinical resistance a prior has only been accomplished once.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE I

Optimis d Parameters of Thre Chemical Mutag ns for E. coli

| Mutagen | Concentration | Treatment Period (min) | Survival (%) | Mutant Frequencies* |
|---------|---------------|------------------------|--------------|---------------------|
| EMS | 2% w/v | 30 | 64 | $1.2 \times 10^{-7}$ |
| NQO | 400 µg/ml | 60 | 77 | $0.6 \times 10^{-8}$ |
| MNNG | 10 µg/ml | 10 | 43 | $1.1 \times 10^{-8}$ |

*Mutants selected for nalidixic acid-resistant ($NA^R$) phenotype. Data are shown from an average of two experiments. Because of slightly better mutant frequency, EMS and MNNG were used in the subsequent mutagenesis experiments.

TABLE II

Point Mutations in QRDR of E. coli by Three Mutagens in Batch Culture

| Mutagen | Mutants | Phenotype | Mutation Achieved in QRDR | Mutation Report in Clinical Isolate |
|---------|---------|-----------|---------------------------|-------------------------------------|
| EMS | NX-E09 | Partially $NA^R$ | Asp-87 (GAC)→ Ile (ATC) | Asp-87→ Ile |
|  | NX-E10 | Completely $NA^R$ | Ser-83 (TCG)→ Leu (TTG) | Ser-83→ Leu |
| NQO | NX-N6 | Completely $NA^R$ | Ser-83 (TCG)→ Leu (TTG) | Ser-83→ Leu |
| MNNG | NX-M3 | Partially $NA^R$ | Asp-87 (GAC)→ Gly (GGC) | Asp-87→ Gly |
|  | NX-M5 | Partially $NA^R$ | Asp-87 (GAC)→ Asn (AAC) | Asp-87→ Asn |
|  | NX-M6 | Partially $NA^R$ | Asp-87 (GAC)→ Gly (GGC) | Asp-87→ Gly |

TABLE III

Point Mutations in QRDR or E. coli by EMS in Continuous Culture

| Mutants | Generations | Phenotype | Mutation Achieved in QRDR | Mutation Report in Clinical Isolate |
|---------|-------------|-----------|---------------------------|-------------------------------------|
| D7NX-E1 | 403 | Completely $NA^R$ | Ser-83 (TCG)→ Leu (TTG) | Ser-83→ Leu |
| D7NX-E2 | 403 | Completely $NA^R$ | Ser-83 (TCG)→ Leu (TTG) | Ser-83→ Leu |

TABLE III-continued

Point Mutations in QRDR or *E. coli* by EMS in Continuous Culture

| Mutants | Generations | Phenotype | Mutation Achieved in QRDR | Mutation Report in Clinical Isolate |
|---|---|---|---|---|
| D3NX-E5 | 135 | Completely $NA^R$ | Ser-83 (TCG)→ Leu (TTG) | Ser-83→ Leu |
| D3NX-E6 | 135 | Completely $NA^R$ | Ser-83 (TCG)→ Leu (TTG) | Ser-83→ Leu |
| D2C2-a | 82 | Partially $NA^R$ | Gly-81 (GGT)→ Cys (TGT) | Gly-81→ Cys |
| D2C2-h | 62 | Partially $NA^R$ | Gly-81 (GGT)→ Cys (TGT) | Gly-81→ Cys |
| D2C2-l | 62 | Partially $NA^R$ | Gly-82 (GAC)→ Asn (AAC) | Not Known |

TABLE IV

Generation of Multi-Drug-Resistant Mutants of *Klebsiella pneumoniae* Containing TEM-1 beta-Lactamase by MNNG in Continuous Culture

| TEM-1 b/a-Containing Strain | Drug-Resistance Phenotype | Expected Mutation |
|---|---|---|
| WT *K. pneumoniae* Tim 19 | $CTX^S$, $CAZ^S$, $FOX^S$, $ATM^S$ | None |
| $CTX^R$ Mutants (8 analyzed) | $CTX^R$, $CAZ^R$, $FOX^R$, $ATM^R$ | TEM-1→ TEM-3 (Gln-39→ Lys Glu-104→ Lys Gly-238→ Ser) |

$^S$= Sensitive, $^R$= Resistant, CTX = Cefotaxime, CAZ = Ceflazidime, FOX = Cefoxitin, ATM = Aztreonum.

References

Dykhuizen, D. E. (1993). "Chemostats used for studying natural selection and adaptive evolution." *Methods Enzymol* 224: 613-31.

Weigel, L. M. C. D. Steward, et al. (1998). "gyrA mutations associated with fluoroquinolone resistance in eight species of Enterobacteriaceae." *Antimicrob Agents Chemother* 42(10): 2661-7.

Arlet, G., M. Rouveau, et al. (1993). "Novel, plasmid-encoded, TEM-derived extended-spectrum beta-lactamase in Kiebsiella pneumoniae conferring higher resistance to aztreonam than to extended-spectrum cephalosporins." *Antimicrob Alents Chemother* 37(9): 2020-3.

What is claimed is:

1. A method of selecting cells resistant to selective agent by inducing directed evolution while applying a selective agent to the cells to determine those cells having resistance.

2. The method according to claim 1, wherein said inducing step includes continuous culturing with the selective agent.

3. The method according to claim 2, wherein said continuous culturing further includes halting the continuous culturing and continuing continuous culturing with the selective agent.

4. The method according to claim 2, wherein said continuous culturing further includes continuously infusing the selective agent.

5. The method according to claim 1, wherein said application step includes culturing the microorganisms in a chemostat.

6. A method of generating mutant drug targets by inducing directed evolution while applying a selective agent to the cells, thereby determining potential drug targets.

7. The method according to claim 6, wherein said continuous culturing further includes halting the continuous culturing and continuing continuous culturing with the selective agent.

8. The method according to claim 7, wherein said continuous culturing further includes infusing continuously the selective agent.

9. The method according to claim 6, wherein said application step includes culturing the microorganisms in a chemostat.

10. A method of determining emerging resistance by inducing directed evolution while applying a selective agent to cells, thereby selecting those microorganisms having emerging resistance.

11. The method according to claim 10, wherein said application step includes continuous culturing with the selective agent.

12. The method according to claim 11, wherein said continuous culturing further includes halting the continuous culturing and continuing continuous culturing with the selective agent.

13. The method according to claim 11, wherein said continuous culturing further includes infusing continuously the selective agent.

14. The method according to claim 10, wherein said application step includes culturing the microorganisms in a chemostat.

15. A method of selecting cells resistant to selective agent by inducing directed evolution while applying a mutagen to the cells to determine those cells having resistance.

16. The method according to claim 15, wherein said inducing step includes continuous culturing with the mutagen.

17. The method according to claim 16, wherein said continuous culturing further includes halting the continuous culturing and continuing continuous culturing with the mutagen.

18. The method according to claim 16, wherein said continuous culturing further includes continuously infusing the mutagen.

19. The method according to claim 15, wherein said application step includes culturing the microorganisms in a chemostat.

* * * * *

SEQUENCE LISTING

```
<160> NUMBER OF SEQ ID NOS: 14

<210> SEQ ID NO 1
<211> LENGTH: 108
<212> TYPE: DNA
<213> ORGANISM: E. coli 11775 (wt)

<400> SEQUENCE: 1
ttggtgacgt aatcggtaaa taccatcccc atggtgactc ggcggtttat gacacgatcg      60
tccgtatggc gcagccattc tcgctgcgtt acatgctggt agacggtc                 108

<210> SEQ ID NO 2
<211> LENGTH: 108
<212> TYPE: DNA
<213> ORGANISM: E. coli

<400> SEQUENCE: 2
ttggtgacgt aatcggtaaa taccatcccc atggtgactc ggcggtttat atcacgatcg      60
tccgtatggc gcagccattc tcgctgcgtt acatgctggt agacggtc                 108

<210> SEQ ID NO 3
<211> LENGTH: 108
<212> TYPE: DNA
<213> ORGANISM: E. coli

<400> SEQUENCE: 3
```
ttggtgacgt aatcggtaaa taccatcccc atggtgactt ggcggtttat gacacgatcg    60
tccgtatggc gcagccattc tcgctgcgtt acatgctggt agacggtc    108

<210> SEQ ID NO 4
<211> LENGTH: 108
<212> TYPE: DNA
<213> ORGANISM: E. coli

<400> SEQUENCE: 4
ttggtgacgt aatcggtaaa taccatcccc atggtgactt ggcggtttat gacacgatcg    60
tccgtatggc gcagccattc tcgctgcgtt acatgctggt agacggtc    108

<210> SEQ ID NO 5
<211> LENGTH: 108
<212> TYPE: DNA
<213> ORGANISM: E. coli

<400> SEQUENCE: 5
ttggtgacgt aatcggtaaa taccatcccc atggtgactc ggcggtttat ggcacgatcg    60
tccgtatggc gcagccattc tcgctgcgtt acatgctggt agacggtc    108

<210> SEQ ID NO 6
<211> LENGTH: 108
<212> TYPE: DNA
<213> ORGANISM: E. coli

<400> SEQUENCE: 6
ttggtgacgt aatcggtaaa taccatcccc atggtgactc ggcggtttat aacacgatcg    60
tccgtatggc gcagccattc tcgctgcgtt acatgctggt agacggtc    108

<210> SEQ ID NO 7
<211> LENGTH: 108
<212> TYPE: DNA
<213> ORGANISM: E. coli

<400> SEQUENCE: 7
ttggtgacgt aatcggtaaa taccatcccc atggtgactc ggcggtttat ggcacgatcg    60
tccgtatggc gcagccattc tcgctgcgtt acatgctggt agacggtc    108

<210> SEQ ID NO 8
<211> LENGTH: 108
<212> TYPE: DNA
<213> ORGANISM: E. coli

<400> SEQUENCE: 8
ttggtgacgt aatcggtaaa taccatcccc atggtgactt ggcggtttat gacacgatcg    60
tccgtatggc gcagccattc tcgctgcgtt acatgctggt agacggtc    108

<210> SEQ ID NO 9
<211> LENGTH: 108
<212> TYPE: DNA
<213> ORGANISM: E. coli

<400> SEQUENCE: 9
ttggtgacgt aatcggtaaa taccatcccc atggtgactt ggcggtttat gacacgatcg    60
tccgtatggc gcagccattc tcgctgcgtt acatgctggt agacggtc    108

<210> SEQ ID NO 10
<211> LENGTH: 108

-continued

```
<212> TYPE: DNA
<213> ORGANISM: E. coli

<400> SEQUENCE: 10
ttggtgacgt aatcggtaaa taccatcccc atggtgactt ggcggtttat gacacgatcg      60
tccgtatggc gcagccattc tcgctgcgtt acatgctggt agacggtc                  108

<210> SEQ ID NO 11
<211> LENGTH: 108
<212> TYPE: DNA
<213> ORGANISM: E. coli

<400> SEQUENCE: 11
ttggtgacgt aatcggtaaa taccatcccc atggtgactt ggcggtttat gacacgatcg      60
tccgtatggc gcagccattc tcgctgcgtt acatgctggt agacggtc                  108

<210> SEQ ID NO 12
<211> LENGTH: 108
<212> TYPE: DNA
<213> ORGANISM: E. coli

<400> SEQUENCE: 12
ttggtgacgt aatcggtaaa taccatcccc attgtgactc ggcggtttat gacacgatcg      60
tccgtatggc gcagccattc tcgctgcgtt acatgctggt agacggtc                  108

<210> SEQ ID NO 13
<211> LENGTH: 108
<212> TYPE: DNA
<213> ORGANISM: E. coli

<400> SEQUENCE: 13
ttggtgacgt aatcggtaaa taccatcccc attgtgactc ggcggtttat gacacgatcg      60
tccgtatggc gcagccattc tcgctgcgtt acatgctggt agacggtc                  108

<210> SEQ ID NO 14
<211> LENGTH: 108
<212> TYPE: DNA
<213> ORGANISM: E. coli

<400> SEQUENCE: 14
ttggtgacgt aatcggtaaa taccatcccc atggtaactc ggcggtttat gacacgatcg      60
tccgtatggc gcagccattc tcgctgcgtt acatgctggt agacggtc                  108
```